| (12) | United States Patent<br>Bernardini et al. | (10) Patent No.: US 9,764,302 B2<br>(45) Date of Patent: Sep. 19, 2017 |
|---|---|---|

(54) PROCESS FOR OBTAINING MICROCAPSULES

(75) Inventors: Marco Bernardini, Casalpusterlengo (IT); Francesca Borgo, Milan (IT); Giorgio Freschi, Piacenza (IT); Edoardo Russo, Piacenza (IT)

(73) Assignee: SIPCAM S.p.A., Milan (IT)

( * ) Notice: Subject to any disclaimer, the term of this patent is extended or adjusted under 35 U.S.C. 154(b) by 579 days.

(21) Appl. No.: 13/464,563

(22) Filed: May 4, 2012

(65) Prior Publication Data

US 2012/0286438 A1 Nov. 15, 2012

(30) Foreign Application Priority Data

May 9, 2011 (IT) .............................. MI2011A0784

(51) Int. Cl.
*B01J 13/16* (2006.01)
*A01N 25/28* (2006.01)
*A61K 31/167* (2006.01)
*A61K 9/50* (2006.01)

(52) U.S. Cl.
CPC .............. *B01J 13/16* (2013.01); *A01N 25/28* (2013.01); *A61K 31/167* (2013.01); *A61K 9/5089* (2013.01)

(58) Field of Classification Search
USPC ........ 428/402–402.24, 403, 404, 407, 321.1, 428/474.4; 427/331, 389.9, 212, 427/213–213.36, 483, 256; 264/534, 5, 264/41, 4–4.7; 424/419, 400, 408, 450, 424/451, 455, 93.7, 184.1, 497, 489, 501, 424/490, 491, 492, 493, 494, 495
See application file for complete search history.

(56) References Cited

U.S. PATENT DOCUMENTS

| 3,577,515 | A | | 5/1971 | Vandegaer |
| 4,936,901 | A | * | 6/1990 | Surgant et al. ............... 504/133 |
| 5,925,464 | A | * | 7/1999 | Mulqueen et al. ........ 428/402.2 |
| 6,001,312 | A | | 12/1999 | Wang et al. |
| 6,652,782 | B1 | | 11/2003 | Budde et al. |
| 2011/0204533 | A1 | * | 8/2011 | Winchester .......... A61K 9/5031 264/4.6 |

FOREIGN PATENT DOCUMENTS

| DE | 19925311 A1 | 11/2000 |
| EP | 0041210 A1 | 12/1981 |
| EP | 0082635 A1 | 6/1983 |
| EP | 0 747 116 A2 | 12/1996 |

OTHER PUBLICATIONS

Rapporto di Recerca from the Ministero dello Svilupo Economic issued in Application No. IT MI20110784, dated Jan. 25, 2012, 3 pages.
European Search Report issued in EP 12166778, dated Jun. 26, 2012.

* cited by examiner

*Primary Examiner* — Marc Zimmer
(74) *Attorney, Agent, or Firm* — Arent Fox LLP

(57) ABSTRACT

A continuous process for preparing microcapsules containing water-insoluble active principles, comprising:
(1) preparing, in a first reactor, an aqueous solution containing one or more surfactants,
(2) preparing, in a second reactor, a solution comprising at least an active principle immiscible in an aqueous phase and a first component for preparing a polycondensation polymer for forming the microcapsule shell,
simultaneously feeding to a tubular reactor of a stream of aqueous solution (1) and solution (2), the ratio of solution (2)/solution (1) being between 0.5 and 2.0,
inletting a stream (3) of a second component for preparing the polycondensation polymer into the reactor, wherein stream (3) reacts with the first component,
wherein the streams are under turbulent flow conditions in the tubular reactor, and are continuously fed to the tubular reactor,
and wherein the ratio between the equivalents of the first component and second component are between 0.9 and 1.1.

17 Claims, No Drawings

PROCESS FOR OBTAINING MICROCAPSULES

The present invention relates to a process for the preparation of microcapsules of active principles having improved productivity compared to the prior art processes and wherein the microcapsules show a substantially homogeneous granulometric distribution.

By substantially homogeneous granulometric distribution of microcapsules it is meant that the b)/a) ratio is comprised between 1.5 and 2.5, wherein b) is the average diameter determined on 90% of the particles and a) is the average diameter determined on 50% of the particles by using the method described hereinafter, the average diameter of 90% of the particles being lower than 15 μm, preferably lower than 12 μm.

Still more specifically the present invention refers to a continuous process having improved productivity in the microencapsulation of water insoluble active principles.

More specifically the present invention regards an improved process for preparing pendimethalin microcapsules having high encapsulation efficiency and improved productivity.

Several processes are known in the art for preparing microcapsules obtained by interfacial polymerization comprising pharmaceutical and agrochemical active principles. See for example EP 747,116 describing a batch process for preparing microcapsules by interfacial polymerization wherein in a first reactor an aqueous solution containing a salt and a surfactant is prepared under stirring; then in a second reactor it is prepared under stirring a solution comprising an active principle, which is immiscible in the salt containing aqueous phase, and the first component (first polycondensation reactant) for preparing the polycondensation polymer forming the microcapsule, then the solution obtained in the second reactor is added under stirring to the aqueous solution of the first reactor to obtain a dispersion; then, under stirring, the second component of the polycondensation polymer (second polycondensation reactant) is added.

From an industrial point of view this process shows several drawbacks as productivity is not high. In fact the second polymer component is added when the dispersion has been formed, by mixing the aqueous phase containing the salt and the surfactant with the solution of the second reactor containing the water immiscible active principle and the first component of the polycondensation polymer. Another disadvantage of this process is that in order to achieve microcapsules having a substantially homogenous granulometric distribution as defined above, the dispersion must be left under stirring for a long time after mixing the solutions coming from the two reactors.

Tests carried out by the Applicant have shown that when stirring is not carried out for a time ranging from about 5 minutes to about 30 minutes, depending on the volume of the solutions to be mixed, the microcapsules obtained do not show a substantially homogeneous granulometric distribution as defined above. From the application point of view, such dispersions are not desirable as they bring to a product wherein the capsules can release the active principle at different times after the field application. Furthermore the reproducibility of these dispersions is stochastic i.e. the composition is not constant and it changes from batch to batch. This makes it difficult the supply to the users an almost constant quality product. In addition the stability of the so prepared microcapsule suspensions could be compromized and in any case it is not high.

Similar processes to that reported above are described, for example, in U.S. Pat. No. 3,577,515. A further drawback of such processes resides in that when isocyanates are used as first polycondensation reactant, known in the art for forming polyurethanes and polyureas, they can react among each other in the presence of an aqueous phase to form prepolymers. This negatively affects the subsequent polycondensation with the second monomer. Example 20 of this patent describes a continuous process wherein it is required that the aqueous phase be preponderant for obtaining an oil in water dispersion.

The need was felt to have available a continuous process for obtaining microcapsules with an high productivity combined with high encapsulation efficiency of the active principle, the microcapsules having a substantially homogeneous granulometric distribution and containing active principles for pharmaceutical and agrochemical use and capable to be prepared with a simple industrial process.

The Applicant has surprisingly and unexpectedly found a continuous process that solves the above technical problem.

An object of the present invention is a continuous process for preparing microcapsules with high productivity, and high encapsulation efficiency of the active principle, the microcapsules showing a substantially homogeneous granulometric distribution and encapsulating water insoluble active principles to be used in the pharmaceutical and agrochemical field, comprising (1) preparation in a first reactor under stirring of an aqueous solution containing one or more surfactants,
(2) preparation in a second reactor under stirring of a solution comprising an active principle immiscible in an aqueous phase, the first monomeric component for preparing the polycondensation polymer forming the microcapsule shell, simultaneous feeding to a tubular reactor of a stream of the aqueous solution prepared in (1) and of a stream of the solution prepared in (2), the ratio stream solution (2)/stream solution (1) ranging from 0.5 to 2.0, the streams of solution (1) and (2) being under turbulent flow conditions in the reactor,
then, optionally, in a time of 0-10 seconds, preferably 0-5, still more preferably 0.5-1, inlet into the reactor under turbulent flow conditions of stream (3) comprising the second monomeric component for preparing the polycondensation polymer,
the ratio between the equivalents (equivalent ratio) between the first monomeric component and the second monomeric component being comprised between 0.9 and 1.1, streams (1), (2) and (3) being continuously fed to the tubular reactor.

As said, by substantially homogeneous granulometric distribution of the microcapsules it is meant that the b)/a) ratio, wherein b) is the average diameter determined on 90% of the particles (microcapsules) and a) is the average diameter determined on 50% of the particles by using the method described later on, is comprised between 1.5 and 2.5 and the average diameter of 90% of the particles is lower than 15 μm, preferably lower than 12 μm.

The polycondensation reaction can take place by using streams (1), (2) and (3).

Streams (1), (2) and (3) have separate inlets into the tubular reactor.

In one embodiment of the process of the invention, the polycondensation reaction can also take place by using only one polycondensation reactant, that is the first monomeric component without the use of the second monomeric component. In this case stream (3) is optional. This occurs for example when the polycondensation reaction is carried out to obtain polyureas. In this case the second component is formed in situ by reaction of the first component, preferably a mixture of isocyanates, with water.

The streams of the reactant solutions fed during the process of the present invention must be under turbulent flow conditions in the tubular reactor.

In general the turbulent flow is achieved when the fluid flow has a high Reynolds number, higher than 2,100 preferably higher than 4,000. For example, for forming a turbulent flow in the tubular reactor fins can be inserted on the reactor walls so that the path of the introduced streams is not linear and vortexes are formed. Another way for obtaining the turbulent flow is to insert in the tubular reactor high shear homogenizers at the stream inlet points. Suitable homogenizers operate for example at rpm comprised between 6,000 and 10,000, preferably 6,000-8,000.

The feeding stream of solution (1) to the reactor preferably ranges from 700 to 1,200 Kg/h, the feeding stream of solution (2) preferably ranges from 1,000 to 1,500 Kg/h, the feeding stream of solution (3) preferably ranges from 70 to 120 l/h.

When desired, each of the single solutions can be fed into the tubular reactor divided into more simultaneous streams, provided that they are fed into the reactor under conditions to render the single stream under turbulent flow in the reactor.

In step (1), if desired, a mixture of surfactants can be used.

The aqueous solution (1) and solution (2) can be introduced into the reactor at a temperature ranging from about 10° C. up to 60° C., preferably from 15° C. to 50° C., depending on the stability of the active principle and on its melting point. For example if the active is liquid at room temperature heating is not necessary, if on the contrary it melts, for example at 50° C., the active principle containing solution is heated to a temperature slightly higher than this.

In the solution (2) one or more actives can be used, optionally one or more organic solvent of the actives can be added. Furthermore, the solution (2) can optionally be prepared divided in two aliquots, one (2a) containing the active principle, optionally an organic solvent, the second (2b) comprising the first monomeric component, optionally dissolved in an organic solvent, the two solutions (2a) and (2b) being continuously premixed and fed into the tubular reactor.

The viscosity of solution (2) is in the range 400-1000 cps, optionally diluting with an organic solvent in case the viscosity is above this limit.

As said, stream (3) comprises the second monomeric component, preferably dissolved in an aqueous solution, which reacts with the first monomeric component to form the polycondensation polymer of the microcapsule shell.

The encapsulation efficiency, determined according to the method reported hereinafter under the "Methods" is ≥96%, preferably ≥98%, more preferably ≥99%.

In order to carry out the crosslinking, in addition to the above mentioned monomers, polyfunctional monomers bearing two or more chemical functions of the same type (for instance, isocyanic) of the first monomer, for example trifunctional monomers, can be used.

The surfactants of solution (1) are selected from anionic surfactants and nonionic surfactants.

Ionic surfactants are preferably selected from the following: sodium ligninsulphonates, for example Reax® 100M and Reax® 88B Ultrazine®NA, calcium ligninsulphonates, for example Borrement®CA, sodium polycarboxylates, for example Geropon® TA 72.

The preferred nonionic surfactants are selected from block copolymers formed by ethoxylated and propoxylated units, for example Pluronic® 10400.

The active principles that can be used in the microcapsule preparation process according to the present invention are preferably agrochemicals and can be selected from herbicides, acaricides, insecticides, fungicides, biocides, plant and insect growth regulators, antidotes.

Among herbicides, there can be mentioned for example those belonging to the classes of dinitroanilines, chloroacetamides, carbamates and diphenylethers. In particular for each of these classes the following ones can be mentioned: Among dinitroanilines: pendimethalin and trifluralin; chloroacetamides: alachlor, acetochlor, dimethenamide, metolachlor, pethoxamide, pretilachlor; carbamates: molinates, triallates, EPTC; diphenylethers: oxyfluorfen.

The following herbicides, not belonging to the above mentioned classes, can also be mentioned: flurochloridone, clomazone, dichlobenil.

Pendimethalin is particularly preferred among herbicides.

Among acaricides, those of the METI class, for example fenazaquin, pyridaben, hexythiazox, can be mentioned.

Among insecticides, those belonging to the classes of pyrethroids, neonicotinoids, carbamates and phosphoorganic compounds can for example be mentioned. In particular for each of these classes the following ones can be mentioned: pyrethroids: bifenthrin, α-cypermethrin, cypermethrin, deltamethrin, imiprothrin, λ-cyhalothrin, pralethrin, tetramethrin, preferably bifenthrin, α-cypermethrin, deltamethrin and λ-cyhalothrin, ethofenprox phosphoorganic compounds: phosmet, chlorpyriphos, naled, fenitrothion; neonicotinoids: imidachloprid, acetamiprid, carbamates: carbosulphan, pirimicarb, aldicarb, thiodicarb, carbofuran and propoxur, preferably carbosulphan, among fungicides, the compounds belonging to the classes of imidazoles, for example imazalil, to the class of triazoles, such as for example tetraconazole, tebuconazole, propiconazole and those belonging to the class of anilinopyrimidines, for example pyrimethanil, can be mentioned.

Among the growth regulators, pyriproxifen can be mentioned.

The active principle in the microcapsule can also be in admixture with other active principles of the same class or of different classes selected among those mentioned above.

The water insoluble polymeric shell of the microcapsule is generally obtainable by reacting the first component with the second component by interfacial polymerization or by reacting the second monomeric component formed in situ with the first monomeric component. The polymers of the microcapsule shell are those obtainable by polycondensation. Polyamides, polyesters, polyurethanes, polyureas can be mentioned.

The most preferred are polyureas.

The first monomeric component, as said, is insoluble in water.

Examples of monomeric components or monomers insoluble in water, in the case when the microcapsule polymer is a polyurea or a polyurethane, are polyisocyanates, for example di- and tri-isocyanates wherein the isocyanate groups are linked to an aliphatic or aromatic group. The following can be mentioned: tetramethylene diisocyanate, pentamethylene diisocyanate, hexamethylene diisocyanate, toluene diisocyanate (TDI), diphenylmethene-4,4'-diisocyanate (MDI), polymethylene polyphenylene isocyanate (PAPI), 2,4,4'-diphenylether triisocyanate, 3,3'-dimetil-4,4'-diphenyl diisocyanate, 3,3'dimethoxy-4,4'-diphenyl diisocyanate, 1,5-naphthylene diisocyanate, 4,4'4"-triphenylmethane triisocyanate.

PAPI has an NCO functionality from 2,3 to 3 and a molecular weight generally comprised in the range 300-400 dalton.

Mixtures of MDI with PAPI or mixtures of MDI, TDI and PAPI are preferred. The isocyanate monomer of solution (2) is preferably MDI in admixture with PAPI in a ratio by weight MDI/PAPI from 100:10 to 20:80, preferably from 35:65 to 65:35. These mixtures are commercially available for example under the trademark Voronate® M220 (Dow), this mixture contains about 40% MDI and 60% PAPI. The ratio by weight MDI/TDI ranges from 10:90 to 100:0, preferably from 30:70 to 100:0.

The second monomeric component of the microcapsule polymer, which is soluble in water, is an aliphatic diamine with a number of carbon atoms from $C_2$ to $C_7$, in particular selected from the following ones: ethylendiamine, propylene-1,3-diamine, tetramethylendiamine, pentamethylen-diamine, 1,6-hexamethyl-enediamine, 1,6-hexamethylendiamine being the preferred one.

In the case of polyureas, the second component for preparing the polycondensation polymer can also not be used. In this case as first and only component a mixture of MDI and TDI is preferably used. As said, in this case the amine is formed in situ when the first monomeric component comes into contact with water.

The polycondensation reaction for obtaining polyamides is carried out by reacting for example a bicarboxylic acid dichloride with a diamine, selected for example from those indicated above for the second monomeric component. For obtaining microcapsules with shell formed by polyesters, a bicarboxylic acid dichloride is reacted with diols.

Other components that can be added to the formulation are for example the following:
thickeners, for example xanthan rubber (Rhodopol®), antifoam agents, as silicone compounds, such as for example Defomex® 1510,
antimould agents, as substituted triazine compounds, for example Amebact® C, and benzoisothiazolinones as Proxel® GXL.

During the preparation of the microcapsules, or successively, after microcapsule formation, alkaline metal inorganic salts, acting as antifreeze and density modulators, can be added, preferably selected from the following: lithium chloride, sodium chloride, potassium chloride, lithium nitrate, sodium nitrate, potassium nitrate, lithium sulphate, sodium sulphate, potassium sulphate, sodium monohydrogen-phosphate, potassium monohydrogen-phosphate, sodium dihydrogen-phosphate, potassium dihydrogen-phosphate and the like; alkaline-earth metal salts, such as magnesium chloride, calcium chloride, magnesium nitrate, calcium nitrate, magnesium sulphate; and ammoniun salts such as ammonium chloride, ammonium sulphate, ammonium monohydrogen-phosphate, ammonium dihydrogen-phosphate, alkaline metal salts of acetic acid.

The preferred salts are chlorides and nitrates, calcium nitrate is still more preferred.

As said, the active in (2) can be added in a solvent, preferably selected from one or more alkylbenzenes having a number of carbon atoms from 9 to 20, preferably from 10 to 16, or esters of lactic acid, biodiesel, etc.

Alkylbenzenes have a boiling point generally in the range from 160° C. to 310° C.; preferably from 165-180° C. to 220-290° C. They are commercially available as Solvesso® 150, Solvesso® 200, Solvesso® 150 ND, Solvesso® 200 ND, preferably in blends free from naphthalene residues such as Solvesso® 150 ND, Solvesso® 200 ND.

The mixture of alkylbenzenes with distillation range from 182-202° C. to 226-284° C. is preferred.

Other solvents such as lactates, for example 2 ethylhexyl-lactate (PurasolvmEHL), or mixtures of vegetable oil esters obtained by transesterification with methanol and ethanol, in particular with methanol, such as biodiesel, can also be used in substitution of alkylbenzenes.

At the end of the microcapsule preparation the maturation step is carried out, for example by heating the microcapsule aqueous suspension to a temperature from 40° C. to 55° C., under a mild stirring, for example at 20 rpm or lower. This step generally lasts from 1 to 5 h. After this step the formulation is completed by adding one or more of the above mentioned additional components. The two processing steps can also be inverted.

As said, the process of the invention allows to prepare microcapsules having improved productivity, high encapsulation efficiency and a substantially homogeneous granulometric distribution as defined above.

The formation of the microcapsules is almost instantaneous after admixing the monomeric components.

It has been found surprising and unexpected that with the continuous process of the invention it would be possible to obtain microcapsules having an improved productivity, high encapsulation efficiency and having a substantially homogeneous granulometric distribution, by operating with feeding streams introduced into the reactor under turbulent flow and optionally by introducing stream (3) in a very short time, comprised in seconds between 0 and 10, preferably 0-5, still more preferably 0-2 and in particular 0.5-1.

It has been unexpectedly and surprisingly found that by operating under continuous conditions according to the process of the invention, by introducing stream (3) into the reactor in so short times with respect to the introduction of streams (1) and (2), no crystallization phenomena of the active take place. This is an advantage of the process of the present invention as it allows to avoid crystallization without the need of adding specific additives, as it occurs in the prior art.

It has furthermore unexpectedly and surprisingly found that by operating under continuous conditions according to the process of the invention, also in the case when the stream (2) of the active and of the first monomeric polycondensation component is in a larger amount with respect to the aqueous solution (1), differently from what indicated in the prior art (see example 20 of U.S. Pat. No. 3,577,515) the encapsulation of the aqueous phase does not take place. See the examples.

The following examples are given for illustrative purposes and are not limiting the scope of the present invention.

EXAMPLES

Methods
Microcapsule Granulometry

The distribution of the microcapsule sizes is measured by a infrared rays Malvern Mastersizer. By this instrument the volumetric distribution of the microcapsules (particles) is determined and the average diameters of the microcapsule fractions corresponding respectively to 50% and 90% of the total microcapsule volume are evaluated.

Viscosity of the Microcapsule Suspension

It is measured at the temperature of 25° C. on the microcapsule suspension as such by a LVT model Brookfield viscosimeter in 2×12 modality.

Encapsulation Efficiency

The encapsulation efficiency is evaluated by contacting a sample of the microcapsule formulation with hexane. This solvent has the property to solubilize the free active principle (a.i.) (not encapsulated) but it is not able to dissolve the polyurea polymer of the microcapsule.

The a.i. extracted with hexane was determined by the analytical methods herein below reported at the following different contact times (minutes) with the solvent: 1,5, 15, 30, 60. A plot was made by reporting in a graph on one axis the time intervals and on the other the amounts of a.i. found in hexane. The value at t=0 gives the amount of a.i. non encapsulated.

The encapsulation efficiency is evaluated by means of the following equation:

$$\frac{\text{(total amount of } a.i.) - \text{(amount of } a.i. \text{ at } t = 0)}{\text{(total amount of } a.i.)} \times 100$$

wherein the total amount of a.i. is the quantity of a.i. added in the microecapsulation process.

The encapsulation efficiency is ≥96%, preferably ≥98%, more preferably ≥99%.

Density

It is measured on the microcapsule suspension by using a DMA 100M densimeter (Mettler Toledo). The determination is carried out in a thermostated cell at 20° C.

Alachlor Determination

The compound is determined according to the CIPAC MT 204/TC/M/3 method by gaschromatographic analysis.

Pendimethalin Determination

The compound is determined according to the CIPAC MT 357/TC/M/3 method by using HPLC analysis.

Acetochlor Determination

The determination is carried out by gaschromatography, by using as internal standard a sample of the compound having a purity of at least 99.9%.

Suspendability

The suspendability is evaluated by the official CIPAC MT 161 method. The microcapsule suspension is diluted with water at 1% w/w and kept in a thermostated bath at 20° C. for 30 minutes. The supernatant is removed by suction and the residue on the bottom of the vessel is dried and weighed. The weight of the residue must be lower than 30% by weight with respect to the starting weight of the microcapsule suspension.

EXAMPLE 1

In a tubular reactor, having the following dimensions: length 11 cm, inner diameter 7.5 cm, by means of pumps and by aid of flowmeters, the following components/solutions are fed:
(1) aqueous solution at 2.6% w/w of sodium ligninsulphonate (Reax® 88B): 1,060 kg/h kept at the temperature of about 50° C.,
(2a) Alachlor, purity 94%: 1,358 kg/h fed as such, at the temperature of about 50° C.,
(2b) hydrophobic monomer mixture polymethylene polyphenyl isocyanate+MDI (PAPI 60%, MDI 40%, average functionality 2.7) (Voronate® M220): 95 kg/h.

The feeding solutions (2a) and (2b) are united in continuous into one stream inletting the tubular reactor, (3) aqueous solution at 40% w/w of hexamethylendiamine, hydrophilic monomer: 91 l/h-7, Feeding solution (3) inlets the tubular reactor at a position located 2 seconds downstream from the inlet (2a)+(2b).

The ratio by weight between streams (2a)+(2b)/(1) is of 1.37.

The feeding solutions inletting the reactor are subjected to a turbulent flow.

The formation of the microcapsules is almost instantaneous. After about 4 hours of run 12,296 kg of aqueous microcapsule suspension were obtained.

The obtained suspension was collected in a tank.

The formulation of the microcapsule suspension is completed by adding the following components, under a mild stirring, in the same tank wherein the subsequent maturation step will take place:

| | |
|---|---|
| $CaCl_2$ | 922 kg |
| NaCl | 494 kg |
| dimethylpolysiloxane (Defomex® 1510) | 30 kg |
| dispersion in water of xanthan rubber Rhodopol® 23 (pregel in water at 2.7%) | 425 kg |

The maturation step has been carried out by maintaining the so obtained formulation under mild stirring at the temperature of about 50° C. for about 3 hours. Then it is cooled to room temperature and on the suspension the following analytical parameters are evaluated:

| | |
|---|---|
| Alachlor | 475 g/L |
| density | 1.13 g/mL |
| granulometry | |
| a) average diameter of 50% of the particles: (microcapsules) | 4.8 μm |
| b) average diameter of 90% of the particles | 9.7 μm |
| Ratio b)/a) | 2 |
| pH | 5.5 |
| suspendability | 85% |
| viscosity | 1600 cps |
| encapsulation efficiency | 99% |

EXAMPLE 2

In the same tubular reactor of example 1, by using pumps and flowmeters, the following components/solutions are fed:
(1) aqueous solution at 2.4% w/w of calcium ligninsulphonate (Borrement® CA): 1,080 kg/h, kept at a temperature of about 50° C.,
(2a) 82,5% w/w of pendimethalin (purity 95%) in Solvesso® 200 ND solvent): 1,040 kg/h, the solution kept at a temperature of about 50° C.,
(2b) hydrophobic monomer mixture polymethylene polyphenyl isocyanate+MDI (Voronate® M220): 73 kg/h, The feeding solutions (2a) and (2b) are united in continuous into one stream inletting the tubular reactor, (3) aqueous solution at 20% w/w of hexamethylendiamine, hydrophilic monomer: 91 l/h, Feeding solution (3) inlets the tubular reactor at a position located 2 seconds downstream from the inlet of (2a)+(2b).

The stream ratio by weight (2a)+(2b)/(1) is of 1.0.

The feeding solutions inletting the reactor are subjected to a turbulent flow.

After about 3 hours of run 9,000 kg of aqueous suspension of microcapsules were obtained.

The obtained suspension was collected in a tank.

The maturation step is then carried out by heating the obtained suspension in a tank at a temperature of 50° C.

under mild stirring for 3 hours. The formulation is then completed by adding the following components:

| | |
|---|---|
| Ca(NO$_3$)$_2$ | 50 kg |
| Amebact ® C | 17 kg |
| Defomex ® 1510 | 18 kg |
| Rhodopol ® 23 (pregel in water at 2.7%) | 380 kg |
| dimethylpolysiloxane (Defomex ® 1510) dispersion in water of xanthan rubber | 30 kg |
| Rhodopol ® 23 (pregel in water at 2.7%) | 425 kg |

It is then cooled down to room temperature and on the suspension the following analytical parameters are then evaluated:

| | |
|---|---|
| pendimethalin | 365 g/l |
| density | 1.13 g/ml |
| granulometry | |
| a) average diameter of 50% of the particles: | 5.8 μm |
| b) average diameter of 90% of the particles: | 9.8 μm |
| ratio b)/a) | 1.7 |
| pH | 8 |
| suspendability | 86% |
| viscosity | 1700 cps |
| encapsulation efficiency | 99% |

EXAMPLE 3

Comparative

In a vessel equipped with stirrer 473.0 g of technical Acetochlor 95% purity are charged under stirring while heating at 50° C. Then, always under stirring, 34.2 g of Voronate® M 220 are added. In the meantime 11 g of dispersant Reax™100M are dispersed in 323 g of water. The organic mixture Acetochlor+Voronate® M 220 is added to the aqueous solution of the dispersant by stirring by a Turrax equipment at 10,000 rpm for about 5 seconds. Then to the so obtained dispersion 14.8 g of an aqueous solution containing 85% by weight of hexamethylendiamine are added.

The mixture is transferred into a reactor kept at 50° C. and added of 50 g of a thickener (pregelled Rhodopol® 23 at 2.7% by weight in water and containing 1 g of Proxel® GXL as antimould agent), 2 g of an antifoam agent Defomex® 1510 and 90 g of calcium nitrate and then the suspension let mature at 4 h at 50° C., as described before.

1 Kg of of microcapsule suspension is obtained.

The suspension is cooled at room temperature and the following analytical parameters are then evaluated:

| | |
|---|---|
| Acetochlor | 495 g/l |
| density | 1.10 g/ml |
| granulometry | |
| a) average diameter of 50% of the particles: | 8.90 μm |
| b) average diameter of 90% of the particles: | 19.03 μm |
| ratio b)/a) | 2.14 |
| pH | 6.5 |
| suspendability | 86% |
| viscosity | 1500 cps |

This comparative example shows that by operating in a batch process and maintaining among the reactants the same weight ratios as in the continuous process, the same temperature conditions, with a mixing time of 5 s between the organic mixture Acetochior+Voronate® (corresponding to stream (2) of the continuous process) and the aqueous solution of the dispersant (corresponding to solution (1) of the continuous process), 90% of the microcapsules shows an average diameter larger than that of the microcapsules of the present invention.

Therefore by operating in batch process under high productivity conditions, using mixing times comparable with those of the examples of the continuous process of the invention, it is not possible to obtain microcapsules having the same characteristics.

EXAMPLE 4

Comparative

Example 3 is repeated but increasing the mixing time of the organic mixture with the aqueous solution of the dispersant in water from 5 seconds to 5 minutes.

1 kg of microcapsule suspension is obtained.

The suspension is cooled at room temperature and analyzed for determining the parameters reported hereunder:

| | |
|---|---|
| Acetochlor | 495 g/l |
| density | 1.10 g/ml |
| granulometry | |
| a) average diameter of 50% of the particles: | 4.75 μm |
| b) average diameter of 90% of the particles: | 9.96 μm |
| ratio b)/a) | 2.14 |
| pH | 6.5 |
| suspendability | 86% |
| viscosity | 1550 cps |

Example 4 comparative shows that with a batch process it is possible to obtain microcapsules having a granulometric distribution and an average size of 90% microcapsules comparable with those obtained with the continuous process of examples 1 and 2 of the present invention, but using a mixing time much longer than that of the examples of the invention, therefore with reduced productivity compared with the claimed continuous process.

EXAMPLE 5

In a tubular reactor having the same dimensions as that used in example 1, by means of pumps and by the aid of flowmeters, the following components/solutions are fed:
  (1) aqueous solution at 2.6% w/w of sodium ligninsulphate (Reax® 88B/:1,060 kg/h kept a a temperature of about 50° C.
  (2a) Alachlor, purity 94%: 1,358 kg/h, fed as such at a temperature of about 50° C.
  (2b) hydrophobic monomer mixture PAPI+MDI (Voronate® M 220: TDI 1:1 w/w: 130 kg/h.

The feeding solutions (2a) and (2B)M are united in continuous into one stream inletting the tubular reactor.

The ratio by weight between streams (2a)+(2b)/(1) is 1.40.

The feeding solutions inletting the r3eactor are subjected to a turbulent flow.

The formation of microcapsules is almost instantaneous. After about 4 hours of run, 12,240 kg of microcapsule aqueous suspension are obtained.

The formulation is then completed and heated as described in example 1.

Analysis on the final microcapsule suspension has given the following results:

| | |
|---|---|
| Alachlor | 472 g/l |
| Density | 1.13 g/ml |
| Granulometry | |
| a) average diameter of 50% of the microcapsules: | 4.5 μm |
| b) average diameter of 90% of microcapsules: | 9.6 μm |
| ratio b)/a) | 2.1 |
| pH | 5.5 |
| viscosity | 1590 cps |
| encapsulation efficiency | 99%. |

The invention claimed is:

1. A continuous process for preparing an aqueous dispersion of microcapsules with an encapsulation efficiency of the active principle ≥98%, the microcapsules showing an homogeneous granulometric distribution as herein below defined and encapsulating water insoluble active principles to be used in the pharmaceutical and agrochemical field, comprising:
   (1) preparation in a first reactor under stirring of an aqueous solution containing one or more surfactants,
   (2) preparation in a second reactor under stirring of a solution comprising an active principle immiscible in an aqueous phase and a first monomeric component,
   simultaneously feeding to a tubular reactor of a stream of the aqueous solution (1) and of a stream of solution (2), the ratio of stream solution (2)/stream solution (1) being between 0.5 and 2.0, the streams (1) and (2) being under turbulent flow conditions in the reactor,
   then, optionally in a time of 0-10 seconds, feeding to the reactor under turbulent flow conditions stream (3) comprising a second monomeric component, the equivalent ratio between the first monomeric component and the second monomeric component being comprised between 0.9 and 1.1,
   streams (1), (2) and (3) being continuously fed to the tubular reactor;
   wherein the substantial homogeneous granulometric distribution of the microcapsules is defined as a b)/a) ratio, wherein b) is the average diameter determined on the smallest 90% of the microcapsules and a) is the average diameter determined on the smallest 50% of the microcapsules, being comprised between 1.5 and 2.5, b) being lower than 15 μm, streams (1), (2), and (3) having separate inlets into the reactor.

2. A process according to claim 1 wherein streams (1), (2) and (3) are used.

3. A process according to claim 1 wherein as first monomeric component a mixture of isocyanates is used.

4. A process according to claim 1 wherein the solution (1) and solution (2) of the active principle and of the first monomeric component are introduced into the reactor at a temperature ranging from 10° C. up to 60° C.

5. A process according to claim 1 wherein solution (2) is prepared by mixing solution (2a) containing the active principle and optionally an organic solvent, and solution (2b) comprising the first monomeric component, optionally dissolved in organic solvent, (2a) and (2b) being continuously premixed and then fed into the tubular reactor.

6. A process according to claim 1 wherein the viscosity of solution (2), optionally diluted with an organic solvent, is in the range 400 and 1000 cps.

7. A process according to claim 1 wherein the surfactants of solution (1) are selected from anionic and nonionic surfactants.

8. A process according to claim 7 wherein the anionic surfactants are selected from the group consisting of sodium ligninsulphonates, calcium ligninsulphonates and sodium polycarboxylates, the nonionic surfactants are selected from block copolymers formed by ethoxylated and propoxylated units.

9. A process according to claim 1 wherein the active principles are selected from herbicides, acaricides, insecticides, fungicides, biocides, plant and insect growth regulators, antidotes.

10. A process according to claim 9, wherein the active principles are selected from the following classes:
    herbicides, selected from the following classes:
       dinitroanilines: pendimethalin and trifluralin
       chloroacetamides: alachlor, acetochlor, dimethenamide, metolachlor, pethoxamide, pretilachlor
       carbammates: molinates, triallates, EPTC;
       diphenylethers: oxyfluorfen, or
       flurochloridone, clomazone, dichlobenil,
    acaricides of the METI class, selected from fenazaquin, pyridaben, hexythiazox,
    insecticides, selected from those belonging to the following classes:
       pyrethroids: bifenthrin, α-cypermethrin, cypermethrin, deltamethrin, imiprothrin, λ-cyhalothrin, prallethrin, tetramethrin, preferably bifenthrin, α-cypermethrin, deltamethrin e λ-cyhalothrin, ethofenprox
       phosphoorganic compounds: phosmet, chlorpyriphos, naled, fenitrothion;
       neonicotinoids: imidachloprid, acetamiprid
       carbammates: carbosulfan, pirimicarb, aldicarb, thiodicarb, carbofuran and propoxur, preferably carbosulfan,
    fungicides, selected from those belonging to the following classes of imidazoles, triazoles, anilinopyrimidine.

11. A process according to claim 10 wherein the herbicide is pendimethalin.

12. A process according to claim 1 wherein the polymeric shell of the microcapsule is obtainable by polycondensation or by reacting the second monomeric component formed in situ with the first monomeric component.

13. A process according to claim 12 wherein the polymer shell is selected from the group of polyamides, polyesters, polyurethanes, polyureas.

14. A process according to claim 12 wherein the polymer is a polyurea or a polyurethane and the first monomeric component is selected between di- and tri-isocyanates wherein the isocyanate groups are linked to an aliphatic or aromatic group and the second component is an aliphatic diamine having $C_2$-$C_7$ carbon atoms.

15. A process according to claim 1 wherein during the preparation of the microcapsule or after the microcapsule formation, ammonium salts, or inorganic alkaline metal salts selected from the following ones are added: lithium chloride, sodium chloride, potassium chloride, lithium nitrate, sodium nitrate, potassium nitrate, lithium sulphate, sodium sulphate, potassium sulphate, sodium monohydrogen-phosphate, potassium monohydrogen phosphate, sodium dihydrogen-phosphate, potassium dihydrogen-phosphate; alkaline-earth metal salts selected from magnesium chloride, calcium chloride, magnesium nitrate, calcium nitrate, magnesium sulphate; and alkaline metal salts of acetic acid.

16. A process according to claim 15 wherein the salt is calcium nitrate.

17. The process of claim 15, wherein the ammonium salts are selected from the group consisting of: ammonium chloride, ammonium sulphate, ammonium monohydrogen phosphate, and ammonium dihydrogen-phosphate.

* * * * *